US00PP21981P2

(12) United States Plant Patent
Giorgerini

(10) Patent No.: US PP21,981 P2
(45) Date of Patent: Jun. 21, 2011

(54) *WISTERIA* PLANT NAMED 'ANGIE'

(50) Latin Name: *Wisteria sinensis*
Varietal Denomination: Angie

(76) Inventor: Angelo Giorgerini, Martinez, CA (US)

( * ) Notice: Subject to any disclaimer, the term of this patent is extended or adjusted under 35 U.S.C. 154(b) by 0 days.

(21) Appl. No.: 12/587,809

(22) Filed: Oct. 13, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

PP4,343 P 12/1978 Hope
PP19,655 P2 1/2009 Tam

*Primary Examiner* — Annette H Para

(57) ABSTRACT

A new cultivar of *Wisteria sinensis* named 'Angie' characterized by strong upright stem growth, characterized by thick non-twining stem growth, large pink and violet flowers and leaf foliage, initially taking a gold color and later changing to bronze and green during a three week period, seed pods are lacking.

2 Drawing Sheets

Botanical classification: *Wisteria sinensis.*
Cultivar designation: 'Angie'.

BACKGROUND OF THE INVENTION

The present invention relates to a new and unique cultivar of *Wisteria* plant. The plant of the present invention lies in the botanical classification of *Wisteria sinensis*. The cultivar bears the name 'Angie' and represents a new Chinese *Wisteria* which vigorously grows as an upright vine.

'Angie' was discovered by the inventor in Concord Calif., a Mediterranean climatic zone, in 1999 as a young plant derived from the plants known as Cook's Chinese *Wisteria*. The cultivar has been asexually reproduced in Martinez, Calif. by a process of layering over a period of ten years and appears to be stable and be reproducible from generation to generation.

SUMMARY OF THE INVENTION

The 'Angie' possesses the following traits which have been observed over a ten year period. The traits distinguish the cultivar of the present invention from other varieties of *Wisteria sinensis* which are known. The 'Angie' exhibits:

1. A strong upright stem growth
2. Pink and violet flowers having banner corollas that are large and erect.
3. Foliage which changes from gold to bronze to green over relatively a long period of time.
4. The lack of seed pods.

'Angie' is a rapid growing plant when young, slowing as the plant matures. The plant blooms in the spring in abundance and retains its bloom for an extended period of time.

5. New stem growth is abnormally thick, with very minimal twining.

BRIEF DESCRIPTION OF THE SEVERAL VIEWS OF THE DRAWING

The accompanying color photographs show the overall of the characteristics of the 'Angie' *Wisteria*. The photographs were taken of a plant approximately nine years old grown outdoors in Martinez Calif.

Photograph in FIG. 1, is a view of the flower of the 'Angie' *Wisteria.*

Figure 1:
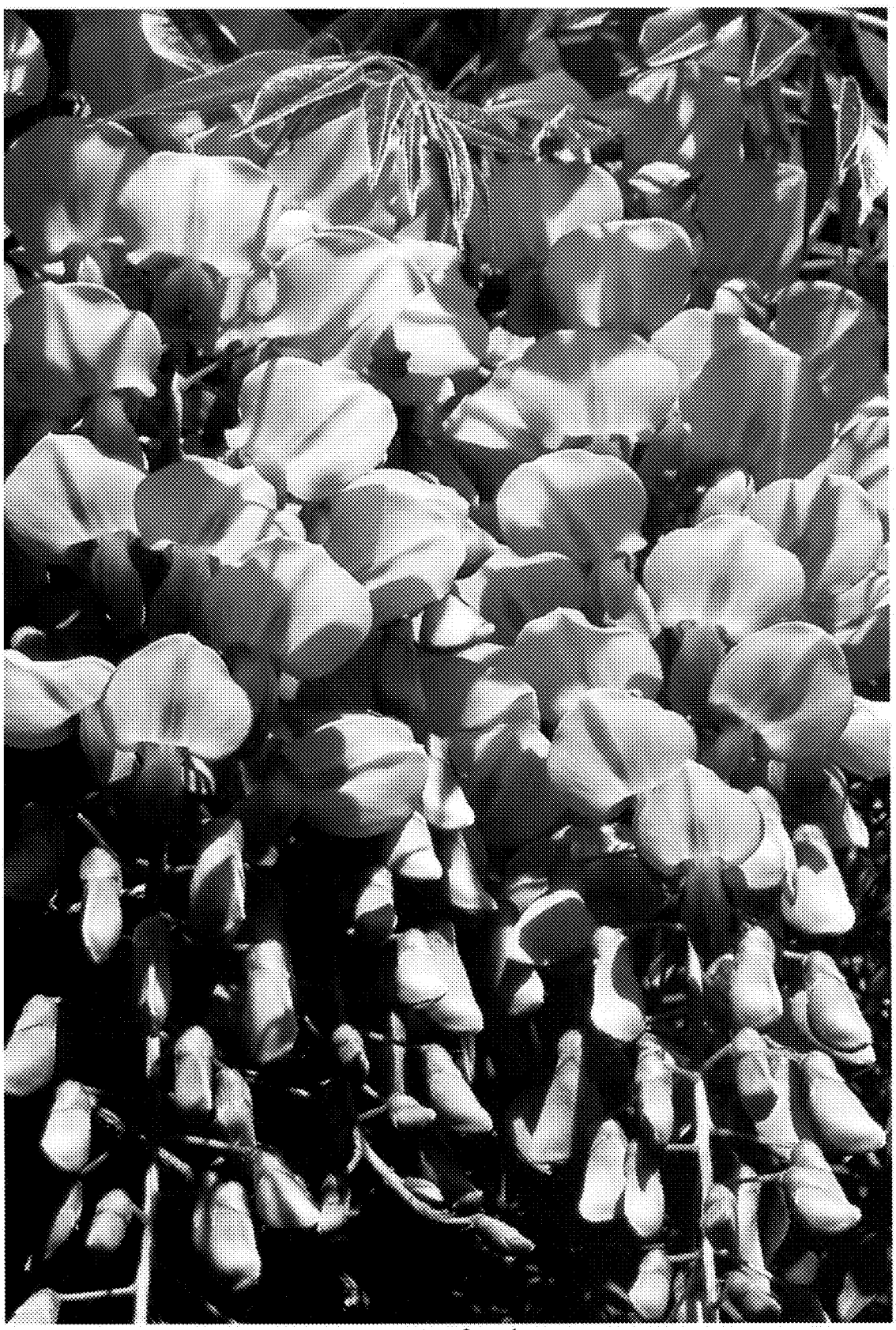
Figure 2:
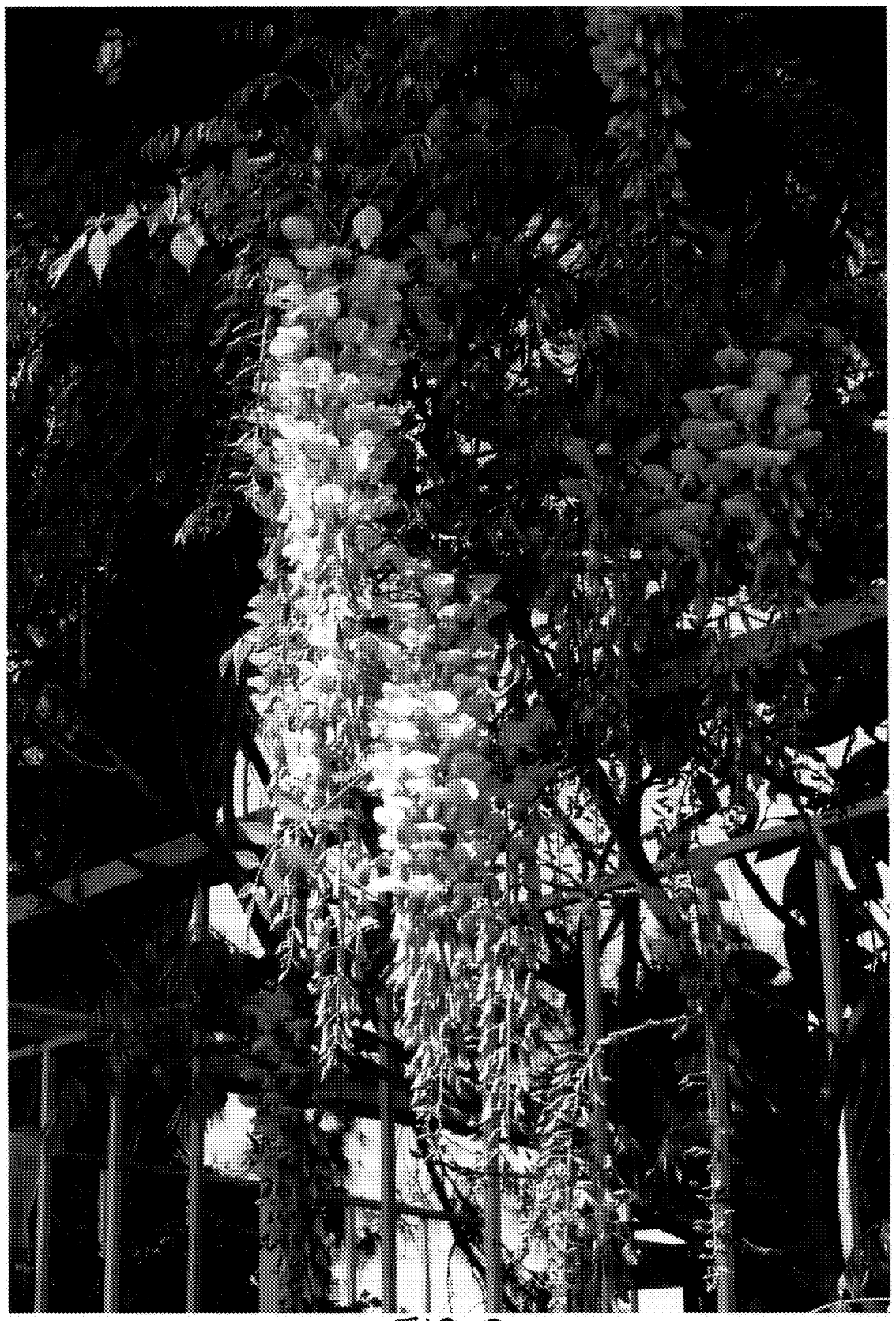

The photograph in FIG. 2, is a view of the overall plant as a vine against a wooden backdrop.

It is believed that the colors in the photographs are accurate in accordance with photography techniques as known to date. The color values cited in the following detailed botanical description are made according to The R.H.S. Colour Chart published by The Royal Horticultural Society, of London England in collaboration with the Flower Counsel of Holland, and represent the actual colors of the 'Angie' *Wisteria.*

DETAILED BOTANICAL DESCRIPTION OF THE PLANT

The following is a detailed description of the cultivar of the present invention grown outdoors in Martinez, Calif. and having an age of about ten years.

Origin: Layering from parent plant.

Botanical classification: 'Angie' is a cultivar of *Wisteria sinensis.*

General description:

- *Growth rate.*—Young plant grows about six inches per year, mature plant reaches a height about 10 feet after about ten years.
- *Plant type.*—Deciduous vine.
- *Cold hardiness.*—U.S.D.A. Zone 5.
- *Blooming characteristics.*—Blooms only in spring.
- *Blooming period.*—Three weeks.
- *Plant habit.*—Erect with minimal support.
- *Roots.*—Coarse.

Growth and propagation:

- *Propagation.*—Layering from parent plant.
- *Shoot appearance.*—Smooth.
- *Growth rate.*—Slow-when young and slowing down when plant matures.

Stem description:

- *Branching.*—Free.
- *Stem diameter.*—3 ml when young and developing into 0.5 cm. when mature. Stem color is 154A when young, 156D when old.

*Stem surface.*—Smooth changing to bark with bumpy surface as plant matures.

*Stem internode length.*—10 to 12 cm.

Foliage description:

*Leaves.*—Ovate to oblanceolate with acuminate tip, internodal length is about 5 cm, 20 to 30 cm in length and 13 through 18 cm in width, 8 to 10 leaves per stem.

*Leaflets.*—Ovate and initially folded along the main vane. The leaflet's upper surface when young color is 30D, leaflet's upper surface mature color is 137C, leaflet's lower surface when young color is 30D, leaflet's upper surface mature color is 137C.

*Petioles.*—4 cm in length, 1.5 ml in width, color is 145A, top surface glabrous, furry when first emerging, bottom is rough.

*Stipules.*—None, but bulbous bottom attachment of petiole to stem.

Flower description:

*Inflorescence.*—Racemes blooms base to end, racemes hang down during bloom.

*Inflorescence duration.*—3 weeks.

*Flower size.*—1.5 cm racemes size up to 38 cm in length and 12 cm across.

*Fragrance.*—Sweet.

*Flower number.*—40 to 60 per raceme.

*Peduncle.*—20 to 30 cm, long color is 144D.

*Petiole.*—2 cm long, color is 33D and 154C.

*Flower buds.*—Ovide shape, color is 155D and 108C.

*Calyx.*—Radiant, but not campanulate, sepal number four each and are tipped at apex, color is 188C.

*Corolla.*—Banner 2.5 cm wide and high and erect, color is 56D and only the spectrum between 108A and 155D wings — number two each, 1.5 cm Long tending to stay enclosed, color is 156A and only the spectrum between 108A and 155D, receptacle — is minimal and color is 56A and only the spectrum between 108A and 155D mottled, corolla faded state color is 69D.

Reproductive organs:

*Pistil.*—Has long furry ovary containing bean-shaped embryos, pistil style color is 145D, pistil has cap-shaped at end of narrowing stalk, stigma color is 158D, ovary color is 145B.

*Stamens.*—Attached to base of ovary, 1 stamen atop of Ovary and 9 joined below, each filament of stamen holds anther which is obilong and segmented, anther color is 163B, while the stamen filament color is 155D.

*Seeds.*—Do not develop into pods, however embryonic Pods develop and shed from plant before maturing.

What is claimed is:

1. A new and distinct cultivar of *Wisteria* plant named 'Angie' as herein now illustrated and described.

* * * * *